US007487606B2

(12) United States Patent
Koo et al.

(10) Patent No.: US 7,487,606 B2
(45) Date of Patent: Feb. 10, 2009

(54) FUNCTIONAL SHOE

(75) Inventors: Sung Jin Koo, Busan (KR); Sung Lae Cho, Busan (KR); Jin Bok Moon, Busan (KR)

(73) Assignee: G-Man Co., Ltd. (KR)

( * ) Notice: Subject to any disclaimer, the term of this patent is extended or adjusted under 35 U.S.C. 154(b) by 482 days.

(21) Appl. No.: 11/403,168

(22) Filed: Apr. 12, 2006

(65) Prior Publication Data

US 2006/0235465 A1 Oct. 19, 2006

(30) Foreign Application Priority Data

Apr. 14, 2005 (KR) ...................... 10-2005-0030874
Dec. 8, 2005 (KR) ...................... 10-2005-0119565

(51) Int. Cl.
*A61F 5/14* (2006.01)

(52) U.S. Cl. ............................................. 36/141; 36/43

(58) Field of Classification Search ................... 36/141, 36/43, 140
See application file for complete search history.

(56) References Cited

U.S. PATENT DOCUMENTS 5,860,229 A * 1/1999 Morgenstern ................ 36/141
7,069,672 B2 * 7/2006 Hahn .......................... 36/141
7,231,730 B1 * 6/2007 Ryan et al. .................... 36/141
7,347,831 B2 * 3/2008 Chiu ........................... 601/15
2004/0111924 A1 * 6/2004 Riccardi ...................... 36/141
2006/0185196 A1 * 8/2006 Wang .......................... 36/141
2008/0005936 A1 * 1/2008 Chiu ............................ 36/3 B
2008/0066343 A1 * 3/2008 Sanabria-Hernandez ....... 36/43
2008/0132811 A1 * 6/2008 Yang et al. .................... 601/30

FOREIGN PATENT DOCUMENTS

KR 1987-002823 8/1987
KR 20-0274120 5/2002
KR 10-0536919 12/2005

* cited by examiner

*Primary Examiner*—Marie Patterson
(74) *Attorney, Agent, or Firm*—St. Onge Steward Johnston & Reens LLC

(57) ABSTRACT

Disclosed herein is a functional shoe, capable of applying micro current to the sole. The shoe includes a micro-current generating part, an acupressure part, and a conduction part. The micro-current generating part is inserted in a side of the shoe, thus generating predetermined micro current and voltage. The acupressure part is made of a conductive material, and is provided on a portion where nerve points of a sole connected to organs in a body are located, thus simultaneously performing physical acupressure action and conduction of micro current. The conduction part is connected between the micro-current generating part and the acupressure part, thus transmitting the generated micro current and voltage to the acupressure part. Thereby, the functional shoe simultaneously performs physical acupressure action on specific nerve points of the sole, and transmits micro current to the nerve points using external force applied when walking.

20 Claims, 12 Drawing Sheets sample dimensions : 10x10x10 load : 60kg generated current : 464 μA sample dimensions : 10x10x10 load : 30kg generated current : 158 μA load : 60kg load : 30kg load : 60kg load : 30kg

FUNCTIONAL SHOE

CROSS-REFERENCE TO RELATED APPLICATIONS

Applicants claim priority benefits under 35 U.S.C. § 119(e) of Korean Patent Application No. 10-2005-0030874 filed Apr. 14, 2005 and Korean Patent Application No. 10-2005-0119565 filed Dec. 8, 2005.

FIELD OF THE INVENTION

The present invention relates, in general, to shoes and, more particularly, to a functional shoe, in which a micro current having a predetermined magnitude is supplied so as to stimulate a human body through the sole when walking, thus providing a physical therapy function.

BACKGROUND OF THE INVENTION

Recently, due to a rise in the standard of living and various desires of consumers, various kinds of shoes having a variety of designs have been manufactured. Further, various special shoes having various functions have come onto the market.

At first, shoes served as means simply for protecting the feet. However, the shoes have been developed so as to be one device having various functions.

That is, the production of shoes having functions suitable for various purposes, for example, safety shoes for special workers, exercise shoes without heels, and shoes for diabetics, has increased.

Meanwhile, according to oriental medicine, acupuncture points interacting with respective organs of the body are distributed throughout the hands and feet.

It is known that internal organs of the body, connected to the acupuncture points, are treated by applying pressure to or stimulating the acupuncture points connected to the hands and feet.

The method of using the acupuncture points distributed throughout the hands and feet has been widely used as indirect and auxiliary therapy for human bodies.

For example, hand acupuncture and foot acupuncture are representative of the method using the acupuncture points. The hand acupuncture and the foot acupuncture treat the body by stimulating respective acupuncture points of the hands and feet connected to specific organs in the body using a needle.

Further, external stimuli for treating the body include acupressure treatment, moxibustion, low frequency treatment, a magnetic field, and electric stimulus, in addition to acupuncture.

In this case, the acupuncture or the acupressure treatment directly stimulates nerves, thus strengthening the activity of nervimotion. Conversely, the low frequency or the magnetic field penetrates into the body, thus performing a special treatment rather than directly stimulating the nerves.

The treatment using the external stimuli originates from oriental medicine. Currently, a substantial effect of the treatment using the external stimuli is demonstrated, so that the treatment has been used in various fields, both in oriental medicine and in western medicine.

Various physical instruments using the methods are prevalent. The methods are applied to shoes, so that they are widely used.

A representative conventional shoe for putting pressure on the sole is made such that the surface of an inner sole laid in the shoe is irregular. In addition to such a shoe, various kinds of functional shoes have been used.

Further, one example of shoes using electricity or a low frequency as external stimuli which are useful for the body is disclosed in Korean U.M. Publication No. 1986-5561, which deals with a shoe having a discharge electrode device.

According to the prior art, a current generated by pressure acting on a piezoelectric actuator is transmitted through a discharge electrode connected via a lead wire.

In this case, the current generated by the piezoelectric actuator is transmitted through the sole. However, the prior art is problematic in that little electricity is applied.

That is, the piezoelectric actuator serves as a storage battery which has a voltage varying with external force. Conversely, when electricity is supplied from the exterior, the pressure of the piezoelectric actuator varies.

The former case is applied to an igniter of a gas range, which uses a variation in pressure. The latter case is applied to electronic equipment, such as an accelerometer, using the variation in pressure.

The aforementioned prior art uses an electric current.

However, the current generated in a conventional piezoelectric sensor is very weak, that is, about several pico-amperes (pA). Meanwhile, the resistance of the sole surface ranges from several hundred ohms (Ω) to several mega-ohms (MΩ). Thus, the prior art is problematic in that little generated micro current is transmitted through the surface of the sole to the interior thereof.

Further, the prior art is problematic in that there is little effect, even though the current is transmitted to the sole.

That is, according to the aforementioned construction, current is conducted through a single discharge electrode, and flows along the shortest distance in view of conduction characteristics. Thus, the current flowing through the single discharge electrode flows along a rectilinear course which is the shortest distance to another discharge electrode. Hence, there is little effect of current acting on the feet.

Due to these problems, the aforementioned construction is impractical, so that it is seldom used.

Further, a shoe having a physical therapy function is disclosed in Korean U.M. Registration No. 20-274120

According to the prior art, a power supply unit is provided in the shoe, so that a low frequency is generated by power supplied from the power supply unit.

However, since the shoe has the following problems, it is useless in actual life.

First, the power supply unit comprises a battery or a structure which must be charged from the outside to supply power.

Such a structure does not consider recovering power when walking, so that much power is consumed. Thereby, a power changing or charging operation is frequently required, thus inconveniencing a user. Hence, it is difficult to use the shoe in actual life.

Second, the shoe comprises a complicated structure having a control part, a low-frequency output part, a low-frequency oscillation part, and others.

A general low-frequency generator is entirely installed in the shoe, so that the space for installing the low-frequency generator in the actual shoe is insufficient. Further, the construction is complicated, so that the shoe may easily malfunction due to external impacts.

Third, the manufacturing cost of the low-frequency generator having the complicated construction is high, thus leading to an increase in the cost of the shoe. Further, the low-frequency generator is heavy, so that the total weight of the shoe is increased.

The heavy shoe goes against the trend towards lighter shoes, so that there is little possibility that the heavy shoe will be used in actual life.

In order to solve the problems, a shoe in which a micro current flows using power generated by applying a force, such as impacts or pressure, to a piezoelectric actuator has been proposed.

For example, according to Korean Patent Appln. No. 10-2005-30874 which was invented by the same inventor, a piezoelectric actuator is provided in a heel portion of the outsole of a shoe. According to the power of the piezoelectric actuator, a micro current is applied to the shoe.

However, the current generated in the conventional piezoelectric sensor is determined depending on the pressure of the sole. A user's weight or an applied impact may be irregular, or pressurization may be slowly performed.

That is, a voltage value and a current value are irregular according to the user's weight or walking manner. In the case where the irregular pressure acts on the piezoelectric actuator, an irregular micro current flows whenever contact occurs.

Meanwhile, the shoe equipped with the low-frequency generator or the shoe applying a micro current using the piezoelectric actuator uses an AC power source. However, a DC power source is mainly used for treatment.

Further, when a user wears the shoe on a rainy day or exercises with the shoe on, he or she wants to stop the flow of the micro current. However, the conventional shoe is problematic in that it is impossible to control the transmission of the micro current as desired.

Further, shoes currently on the market currently have only a simple single function. The shoes do not efficiently demonstrate their functions.

Therefore, if a shoe which has multiple functions and can be used for medical treatment is produced, the shoe is not merely a means for protecting the foot, but can be used as the auxiliary means for several treatments which are useful for the body in daily life.

SUMMARY OF THE INVENTION

Accordingly, the present invention has been made keeping in mind the above problems occurring in the prior art, and an object of the present invention is to provide a shoe, which has a complex and multiple function, thus providing a physical therapy function.

Another object of the present invention is to provide a shoe, which generates its own electrical energy using a force generated by a person's exercise, and converts the electrical energy into various physical energy, thus producing permanent energy.

A further object of the present invention is to provide a shoe, which directly applies physical energy to nerve points that are distributed on the sole and are connected to respective organs in the body, thus transmitting stimulus helpful for the body through the nerves.

Yet another object of the present invention is to provide a shoe, which is capable of intermittently supplying a micro current using power fed from a battery.

A still further object of the present invention is to provide a shoe, which is constructed to control the on/off operation of a micro current at the exterior, as desired.

In order to accomplish the objects, the present invention provides a functional shoe, including a micro-current generating part inserted in a side of the shoe, thus generating predetermined micro current and voltage; an acupressure part made of a conductive material, and provided on a portion where nerve points of a sole connected to organs in a body are located, thus simultaneously performing physical acupressure action and conduction of micro current; and a conduction part connected between the micro-current generating part and the acupressure part, thus transmitting the generated micro current and voltage to the acupressure part. The functional shoe simultaneously performs physical acupressure action on specific nerve points of the sole, and transmits micro current to the nerve points, using external force applied when walking.

According to the first aspect of this invention, the micro-current generating part comprises a piezoelectric actuator which instantaneously generates micro current and voltage using external force.

Further, the micro-current generating part generates instantaneous current of 300 μA or less and instantaneous voltage of 50V or less, when an instantaneous external force of 3 kg to 150 kg is applied.

The piezoelectric actuator is provided under the acupressure part, and is connected to the acupressure part via the conduction part.

According to the second aspect of this invention, the micro-current generating part includes a battery to supply DC power; a micro-current generating circuit to convert the DC power supplied from the battery into micro current; and a switch unit protruding from a predetermined portion on a bottom surface contacting a sole, pressed by an external force, and performing a switching operation at predetermined timing by the external force, thus controlling power supplied from the battery to the micro-current generating part, at an exterior.

Preferably, the micro-current generating circuit is constructed so that power supplied from the battery is electrically connected to a condenser, resistors, and a variable resistor, so that, when the switch unit is turned on by an external force, the power supplied from the battery flows to the variable resistor to charge the condenser, and simultaneously is applied to a collector of the transistor, and current flowing to the variable resistor flows to a base of the transistor in proportion to a voltage drop occurring in the resistors until the condenser is charged, and thereafter, when the condenser has been charged, the condenser serves as a decoupling condenser, so that current is applied to the base of the transistor, thus generating micro current.

The micro-current generating part generates micro current using internal resistance of the acupressure part.

Preferably, the switch unit includes an insert groove formed through a side of an outsole of the shoe; a push button inserted into the insert groove, and protruding from a bottom surface of the outsole so that the push button is moved up and down by a user's sole; a power-input contact point installed under the push button, and made of a conductive material; and a spring installed between the outsole and the push button, thus elastically restoring the push button to an original state thereof, when the external force is eliminated.

The switch unit further includes a timing circuit detecting a trigger signal when the switch unit has contacted the battery, and detecting a reset signal when a predetermined time has passed, micro current flows for a predetermined time, and an external force is applied, thus resetting a timer operation. Thus, when the external force is applied, the reset signal is sent, and when the external force is removed, the trigger signal is sent, so that the driving of the micro-current generating part is controlled by the timing circuit.

The switch unit further includes a manual switch which is provided at an upper on an outer surface of the shoe and controls power supply from the battery.

Preferably, the micro-current generating part is provided on a heel portion of the shoe.

Preferably, the acupressure part comprises a magnet, thus providing stimulus using magnetism.

Preferably, the conduction part connects the micro-current generating part to the acupressure part in parallel.

Further, the conduction part connects the micro-current generating part to the acupressure part in series.

According to the third aspect of this invention, a functional shoe includes a main body; and an inner sole, having a micro-current generating part comprising a piezoelectric actuator which instantaneously generates micro current and voltage using external force, a plurality of acupressure parts made of a conductive material, and provided on portions corresponding to nerve points of a sole connected to organs in a body, and a conduction part connected between the micro-current generating part and each of the acupressure parts, thus transmitting the generated micro current and voltage to each of the acupressure parts. In this case, the inner sole is detachably mounted to the main body. Alternatively, the functional part may be directly provided on an outsole integrated with the main body of the shoe.

As described above, according to the present invention, a physical stimulus, a magnetic force, and a micro current act together through acupressure parts provided on a sole of a shoe, thus stimulating nerve points of the sole, therefore promoting blood circulation, and affecting organs in the body to promote the health.

Further, according to the present invention, a shoe is provided with a battery, thus intermittently supplying a micro current, therefore reducing the required power supply capability of the battery by as much as half. Further, the shoe according to the present invention is capable of using a rechargeable battery, thus reducing maintenance costs.

According to the present invention, it is possible to control the flow of a micro current transmitted to the sole, as desired.

DESCRIPTION OF REFERENCE CHARACTERS OF IMPORTANT PARTS

| | |
|---|---|
| 1. outsole of a shoe | 2. upper |
| 100. micro-current generating part | 100a. case |
| 110. battery | 120. micro-current generating part |
| 130. switch unit | 130a. insert groove |
| 130b. push button | 130c. elastic member |
| 130d. power-input contact point | 132. timing circuit |
| 132a. lead wire | 134. manual switch |
| 200(210, 220, 230, 240). acupressure parts | |
| 210a, 220a, 230a, 240a, 210b, 220b, 230b, 240b. acupressure rods | |

DETAILED DESCRIPTION OF THE INVENTION

Hereinafter, a shoe according to the present invention constructed as described above will be described in detail with reference to the accompanying drawings.

First, the nerve distribution in the sole will be described with reference to FIG. 1.

Figure 1:
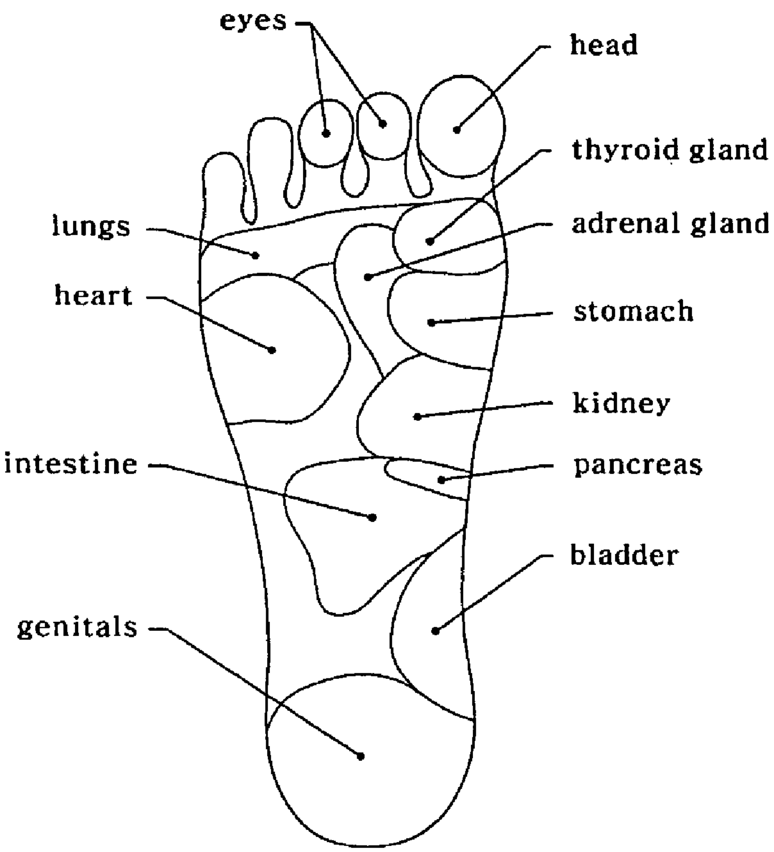
FIG. 1 is a view showing portions of meridian pathways in the sole, which are connected with organs in the body.

FIG. 1 shows nerve points in the sole, which are correlated with respective organs in the body.

Such distribution of the nerve points has not been clearly acknowledged by western medicine yet, but is widely used in oriental medicine. The nerve points are widely used in actual life in foot acupuncture and foot massage.

The drawing shows the positions of the nerve points connected with respective organs in the body.

For example, diabetes is caused by trouble related to insulin secretion. Thus, a region around a nerve point corresponding to the pancreas is stimulated. Further, when a person has a digestive trouble, a nerve point corresponding to the stomach is stimulated.

Since the nerve distribution diagram based on oriental medicine is widely known to people, it will not be described in detail below.

Figure 2:
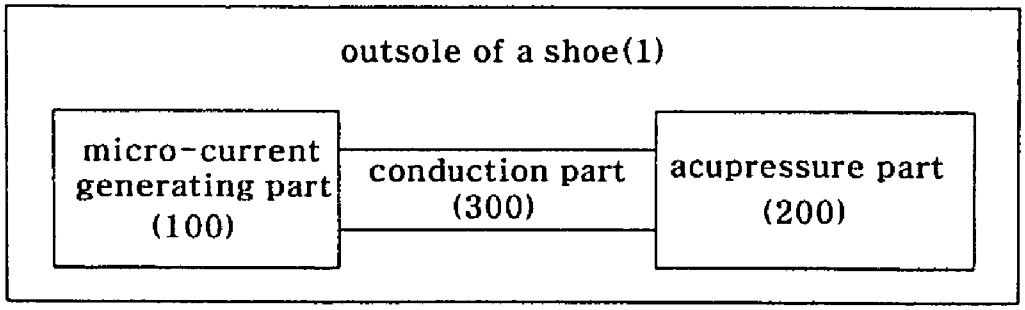
FIG. 2 is a view illustrating the concept of a functional shoe, according to the first embodiment of the present invention.
Figure 3:
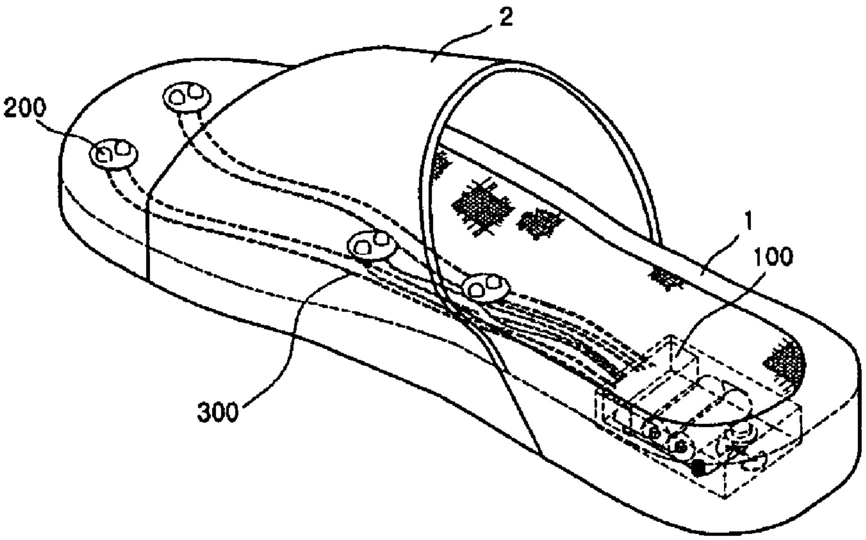
FIG. 3 is a perspective view showing the interior of the functional shoe, according to the first embodiment of this invention.

FIG. 2 is a view showing the concept of a functional shoe, according to the present invention, and FIG. 3 is a perspective view showing the interior of the functional shoe, according to the present invention.

As shown in the drawings, the functional shoe according to this invention is divided into three parts.

That is, the functional shoe includes a micro-current generating part 100, an acupressure part 200, and a conduction part 300. The micro-current generating part 100 is provided at a predetermined position on the shoe, and generates a predetermined micro current and voltage. The acupressure part 200 is made of a conductive material, and is provided at a position where the nerve points of the sole, connected to the organs in the body, are located, thus simultaneously performing physical acupressure and conduction of a micro current. The conduction part 300 is connected between the micro-current generating part 100 and the acupressure part 200, and transmits generated micro current and voltage to the acupressure part 200.

The present invention may be classified into the first embodiment and the second embodiment. According to the first embodiment, the micro-current generating part 100 comprises a piezoelectric actuator which generates instantaneous current and voltage using external force. According to the second embodiment, the micro-current generating part 100 supplies power through a battery, thus supplying micro current in a micro-current generating circuit.

FIG. 3 is a view showing the functional shoe, according to the first embodiment of the present invention.

Generally, the shoe includes an outsole 1 and an upper 2. The outsole 1 is fabricated to correspond to the shape of a person's foot. The upper 2 extends upwards from the edge of the outsole 1 to surround his or her foot, and defines the external appearance of the shoe.

The micro-current generating part 100 according to the first embodiment of this invention is the piezoelectric actuator.

The piezoelectric actuator is an actuator, in which positive and negative charges are produced on both surfaces of a crystalline plate in proportion to external force, when pressure acts on the crystalline plate in a predetermined direction.

That is, when external pressure is applied to the piezoelectric actuator, the piezoelectric actuator produces voltage and current. The intensity of voltage and the quantity of current produced by the piezoelectric actuator increase in proportion to external pressure.

The power source for driving the piezoelectric actuator results from a user's exercise, such as walking or running.

That is, pressure transmitted through the sole when a user moves while wearing the shoe is used.

Thus, the piezoelectric actuator is located in the outsole or an inner sole, which form the shoe. The position of the piezoelectric actuator is set to the heel portion or the bottom of the anterior region of the shoe.

Of course, as shown in FIG. 3, when the piezoelectric actuator is located in the heel portion of the shoe, the highest pressure is produced. Thus, in this case, the quantity of electrical energy is the largest.

Further, the voltage and the current of the piezoelectric actuator change according to the material, size, and shape of the piezoelectric actuator. However, it is possible to produce instantaneous voltage of several volts to several thousand volts (V). Generally, it is known that the quantity of such current is very small, that is, several pico-amperes (pA).

However, since the quantity of current produced in the piezoelectric actuator is little, it is impossible to provide an effective electric stimulus.

Thus, the piezoelectric actuator according to this invention generates a micro current that is higher than several micro-amperes (μA), which is useful as an electric stimulus. It is necessary to produce relatively high instantaneous voltage of several tens or hundreds of volts (V), so that the micro current can be conducted into the body through the sole, which has relatively high resistance. The reason will be described below.

Generally, it is known that a micro current of about 0.06 mA flows in the body, the intensity of the micro current changing depending on a person's state of health.

Further, it is clinically known that a smaller quantity of micro current flows in the body when a person's health is poor.

Thus, the micro current having intensity suitable for stimulating the body is supplied from the exterior, thus contributing to balance in the body.

Further, it is known that a person can perceive current of about 1 mA, which may vary slightly according to variation in perceptive capability. It is undesirable for current to flow for a lengthy period of time.

Thus, it is suitable for the current supplied through the sole to have an intensity of several to several hundred micro-amperes (μA), which is less than 1 mA. Preferably, the current does not flow continuously but flows intermittently, thus serving as a stimulus.

It is most preferable that the instantaneous current of the micro current be 60 μA or less, because this does not cause harmful effects even if the micro current is transmitted for a lengthy period of time.

Further, as described above, it is known that the surface resistance of the sole is 500Ω to several mega-ohms (MΩ).

The surface resistance of the sole varies according to the body's condition. In the dry state, the sole has a resistance of several mega-ohms (MΩ). Meanwhile, in the fully wet state, the sole has a resistance of about 500Ω.

Thus, when the sole has high surface resistance of several mega-ohms (MΩ), high voltage is instantaneously required so that the micro current overcomes the high resistance and is transmitted into the body through the sole.

For example, when the surface resistance of the sole is 5 MΩ, the instantaneous voltage must be 50V or higher to allow the micro current of 10 μA to be applied.

Such a high voltage also serves as a stimulus.

However, the excessive flow of current leads to a problem in the body. Thus, if the quantity of micro current is correct, relatively high voltage serves as the stimulus which allows the micro current to be easily transmitted through the sole into the body.

Therefore, the piezoelectric actuator used in the present invention produces instantaneous current of several to several tens of micro-amperes (μA) by an external pressure. It is preferable that instantaneous current be 300 μA or less.

At this time, the instantaneous voltage is several to several hundreds of volts (V). It is preferable that instantaneous voltage be 50V or less.

However, it is difficult for a general piezoelectric actuator to achieve a current value and a voltage value which are required to perform the stimulus function required in this invention.

That is, the general piezoelectric actuator is operated by the pressure produced when walking, thus generating instantaneous current and instantaneous voltage. However, the quantity of the generated instantaneous current is too small, that is, on the pico-ampere (pA) scale, thereby it is difficult to satisfy the requirements of this invention.

As described above, the piezoelectric actuator is used as a sensor or a displacement control device. In this case, the vibration of the piezoelectric sensor according to the variation in external current and voltage is mainly used. Thus, the generation of current is seldom considered.

Therefore, the piezoelectric actuator must be deformed so that the piezoelectric actuator produces required current and voltage according to the external pressure, as in the present invention.

Thus, the piezoelectric actuator used in this invention is a PZT-based piezoelectric ceramic, and the composition of the piezoelectric actuator comprises a raw material compound consisting of $PbO2$, $TiO2$, $ZrO2$, $MgO$, and $Nb2O2$. The raw material compound is fabricated as a ceramic sheet through tape casting.

Further, several tens of ceramic sheets fabricated in this way are layered up, and the layered piezoelectric material is sintered. Thereby, a required piezoelectric actuator is obtained.

When the piezoelectric actuator manufactured in this way produces current of several tens of micro-amperes (μA), as is required in the present invention, the following conditions must be considered.

The piezoelectric coefficient (d) measurable in the piezoelectric material is calculated according to the following equation.

$d=(Q/A)/(F/A)=Q/F$ (Q: quantity of electric charge produced in the piezoelectric material, A: area subjected to force applied from the piezoelectric material, F: force applied from the piezoelectric material)

In this case, the piezoelectric coefficient (d) is the quantity of electric charge which is produced by the force applied to the piezoelectric material.

For example, when a person having a weight of 50 kg walks, pressure applied to the sole is equal to 120% of the weight, that is, a load of about 60 kg, when walking normally. Meanwhile, when walking rapidly, a force corresponding to 135% of the weight is applied to the sole. Further, when running, a force corresponding to 200% of the weight is applied to the sole.

Thus, in the case of walking normally, a load of about 60 kg acts, so that the force applied by the sole is calculated according to the following equation.

$F=ma=60$ kg×9.8 m/s2. Thus, the force is approximately 600N.

Further, when the force of 600N is applied to the PZT-based piezoelectric ceramic having the piezoelectric coefficient d of 500 pC/N, the quantity of electric charge is equal to 500 pC/N×600N=3×10−7 C (C: coulomb, pC: pico-coulomb).

Assuming that the time during which the sole contacts the ground and a force acts is 1 second(s), the generated instantaneous current (I) is calculated according to the equation.

$$I=dQ/dT=3\times10^{-7}\ \text{C}/1\ \text{s}=0.3\ \mu\text{A}$$

Thus, when the layered piezoelectric ceramic is used as the piezoelectric material, the quantity of electric charge is increased in proportion to area subjected to an external force. Thus, the current is increased according to the number of layers of the piezoelectric ceramic.

Theoretically, when the piezoelectric ceramic is stacked 100 layers high, a current of about 30 μA is produced.

Figure 4:
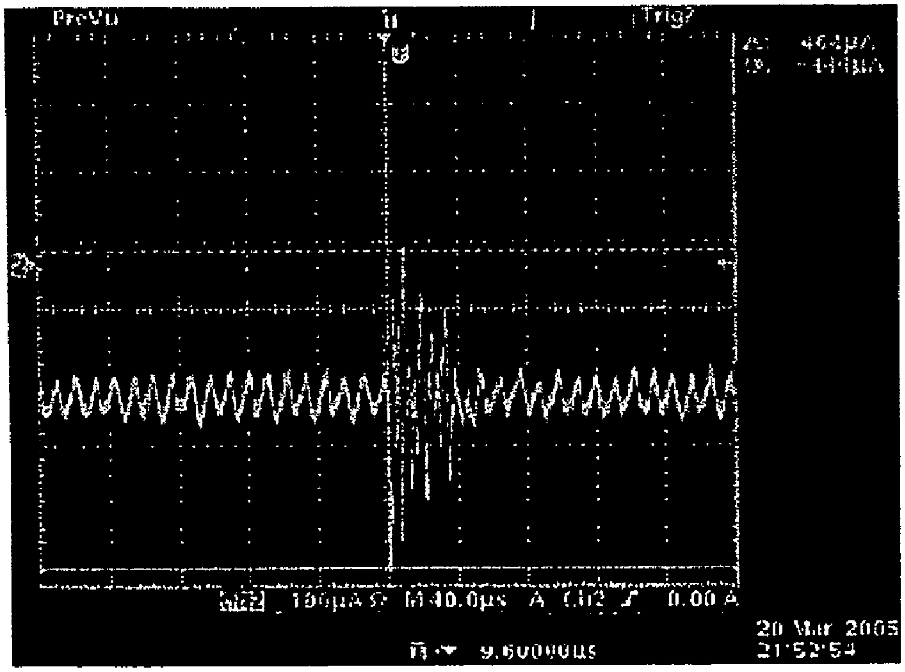
FIG. 4 is a graph showing a measured value (464 $\mu$A) of an instantaneously generated current corresponding to a load (about 60 kg) applied to a piezoelectric actuator, according to the present invention.
Figure 5:
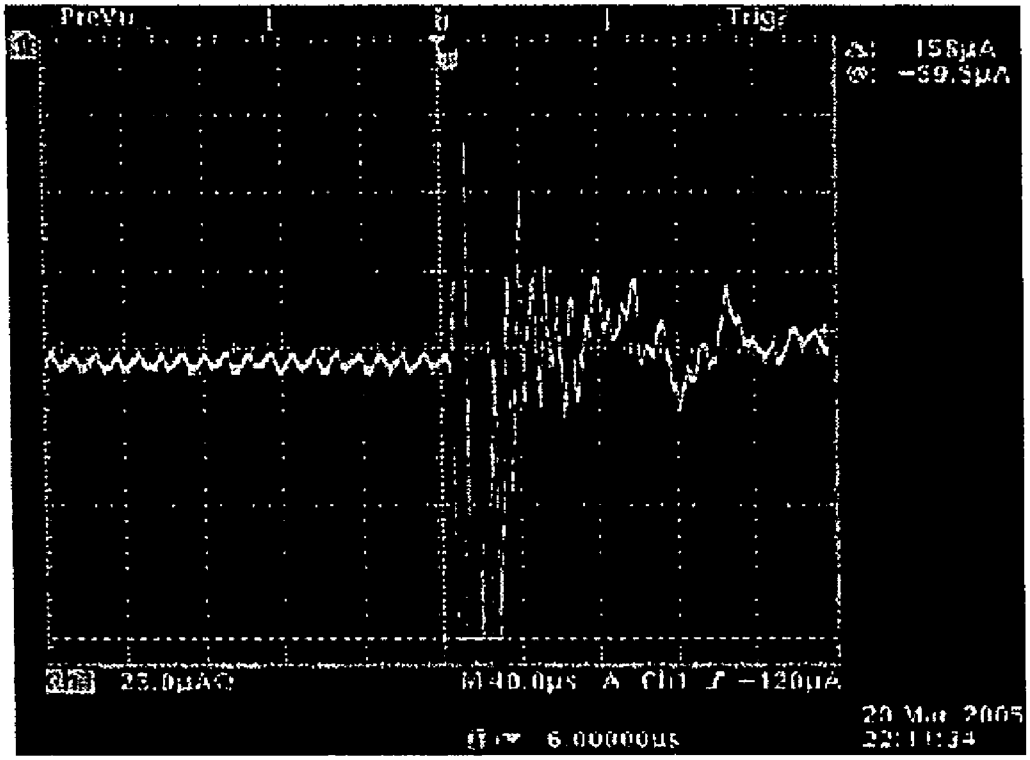
FIG. 5 is a graph showing a measured value (158 $\mu$A) of an instantaneously generated current corresponding to a load (about 30 kg) applied to the piezoelectric actuator, according to the present invention.
Figure 6:
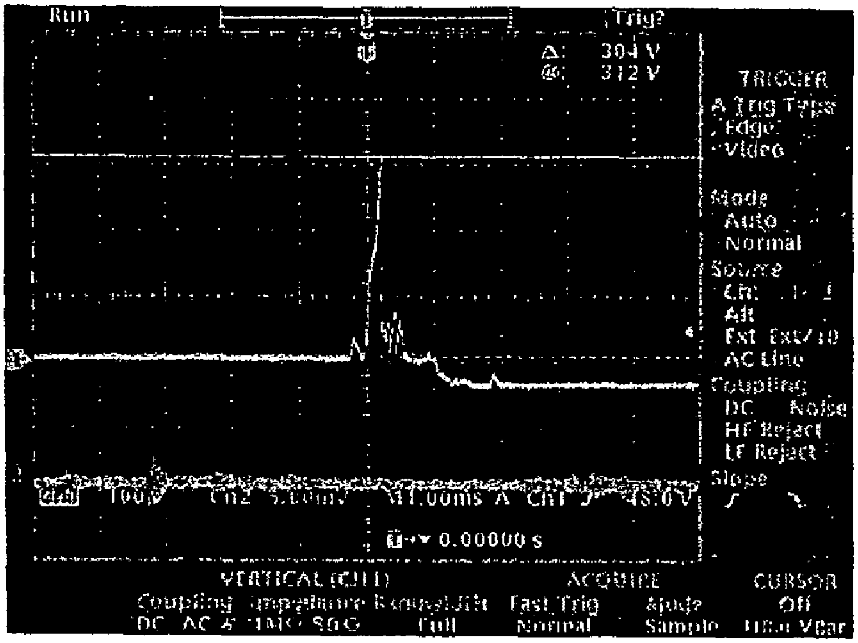
FIG. 6 is a graph showing a measured value (304V) of an instantaneous voltage corresponding to a load (about 60 kg) applied to the pure piezoelectric actuator, before the piezoelectric actuator of the invention is installed in a shoe.
Figure 7:
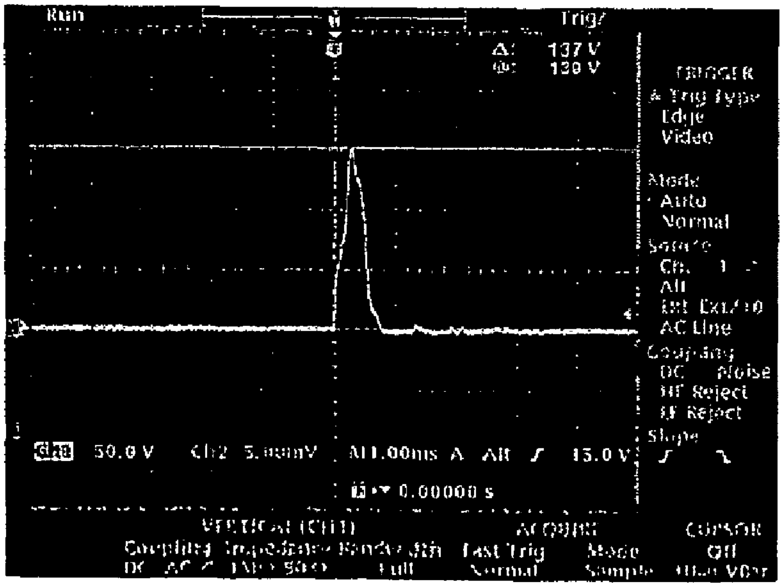
FIG. 7 is a graph showing a measured value (137V) of an instantaneous voltage corresponding to a load (about 30 kg) applied to the pure piezoelectric actuator, before the piezoelectric actuator of the invention is installed in the shoe.
Figure 8:
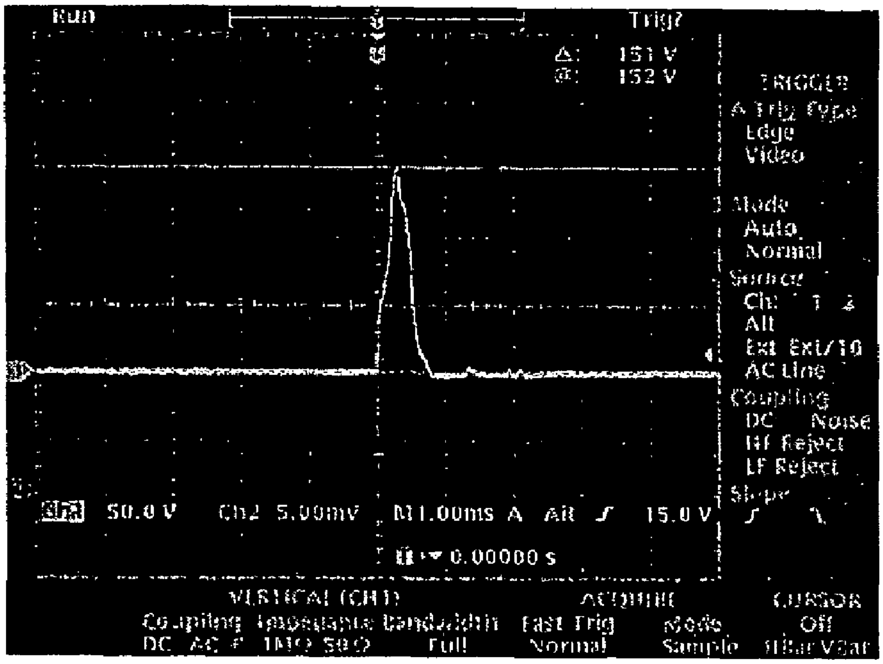
FIG. 8 is a graph showing a measured value (151V) of an instantaneous voltage corresponding to an applied load (about 60 kg), after the piezoelectric actuator of the invention is installed in the shoe.
Figure 9:
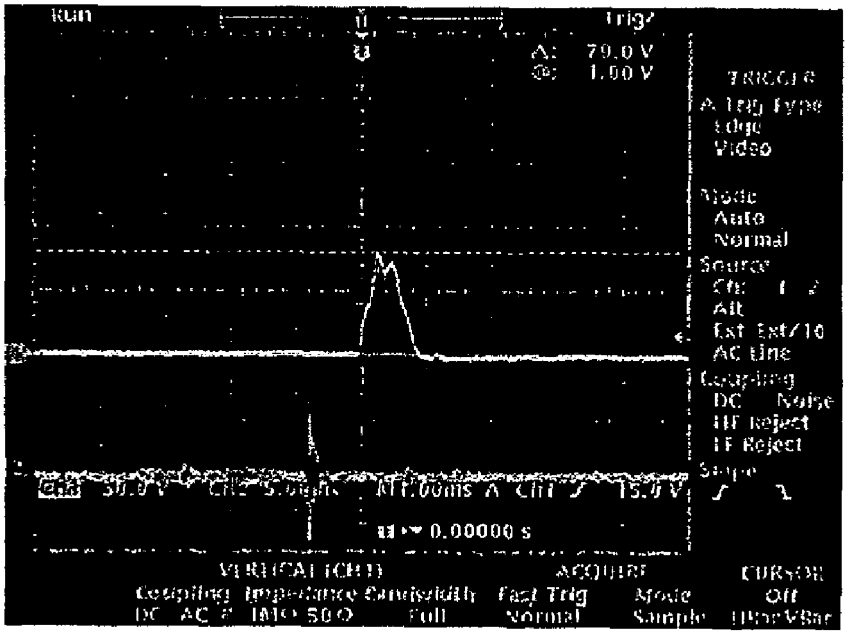
FIG. 9 is a graph showing a measured value (79V) of an instantaneous voltage corresponding to an applied load (about 30 kg), after the piezoelectric actuator of the invention is installed in the shoe.

In order to evaluate the theoretical suitability, the inventor of the present invention performed a field test using a layered piezoelectric actuator having a size of 10 mm wide by 10 mm long by 10 mm high. The result is represented in FIGS. 4 and 5.

As shown in the drawings, the test result is as follow. That is, as shown in FIG. 4, when a load of about 60 kg is instantaneously applied to the layered piezoelectric actuator for about 0.1 second, an instantaneous current of about 464 μA is produced. Further, as shown in FIG. 5, when a load of about 30 kg is applied, an instantaneous current of about 158 μA is produced.

This shows that the piezoelectric actuator produced instantaneous current which exceeded the value required to stimulate a specific region of the sole in the present invention, and thus is sufficiently applicable to the shoe.

Meanwhile, the generation of proper instantaneous voltage is an indispensable requirement so that the piezoelectric actuator can serve as an electric stimulus.

The instantaneous voltage required for the piezoelectric actuator must be several to several hundreds of volts (V). In the present invention, the piezoelectric actuator is adapted to the shoe, so the situation of the piezoelectric actuator actually being mounted to the shoe must be considered.

Generally, the outsole of the shoe is made of a synthetic resin material having proper elasticity to mitigate shocks to some degree.

In consideration of the conditions, according to this invention, the piezoelectric actuator is installed on an ethylene vinyl acetate (EVA) sole, which is widely used as an outsole for a shoe. In such a state, the test was performed.

As known from the results of FIGS. 6 to 9, when the piezoelectric actuator is an existing pure piezoelectric actuator, and a load of about 60 kg is applied, an instantaneous voltage of about 304V is produced. Meanwhile, when a load of about 30 kg is applied, an instantaneous voltage of about 137V is produced.

However, when the piezoelectric actuator of this invention is installed in the shoe sole, and a user actually walks with the shoe on, the measured result of generated voltage is as follows. That is, when a load of about 60 kg is applied, an instantaneous voltage of about 151V is produced. Meanwhile, when a load of about 30 kg is applied, an instantaneous voltage of about 79V is produced. Thus, in comparison with the existing pure piezoelectric actuator, the piezoelectric actuator of this invention has a little voltage drop.

This result is obtained because the shoe sole has predetermined elasticity that absorbs external force to some extent. Such a result is sufficient to be applied to the shoe as the micro current stimulus.

Meanwhile, according to the first embodiment of this invention, the piezoelectric actuator used as the micro-current generating part 100 generates instantaneous current and voltage which are produced by the external force applied to the sole. Thus, the piezoelectric actuator does not have a fixed form, but the quantity of the generated current and voltage is changed according to the applied external force. The piezoelectric actuator generates AC current.

That is, the piezoelectric actuator operates variably according to the person's weight and walking manner (walking, running, etc.). Whenever varying pressure is applied to the piezoelectric actuator, the value of the instantaneous voltage or current varies.

That is, the magnitude of voltage output from the piezoelectric actuator is in proportion to the magnitude of pressure. The wave form of voltage has various forms, including an impulse form. Moreover, an undesirable harmonic wave may be formed.

Thus, excessive voltage may be produced by the piezoelectric actuator.

In this case, it is necessary to limit excessive voltage, which unsuitable for the body, in addition to limiting undesirable harmonic waves and deformed voltage waveforms.

For such a conversion, the present invention requires a conversion part which converts voltage and current output from the piezoelectric actuator.

The conversion part may have various forms. For example, the conversion part may regulate the magnitude of voltage or eliminate harmonic waves using the simplest passive low-pass filter. The low-pass filter follows the following equation.

$$f=\frac{1}{2\pi CR}$$ (C: condenser, R: resistance)

The cutoff frequency that is filtered by the low-pass filter and output therefrom depends on the condenser C and the resistance R. In order to lower the cutoff frequency, the condenser C and the resistance R only have to increase.

If the primary low-pass filter is insufficient, secondary and tertiary low-pass filters are designed to provide a low-pass filter which performs the most appropriate filtering.

Thus, the condenser C and the resistance R are appropriately constructed, thus limiting the magnitude of the current and voltage output from the piezoelectric actuator.

However, generally, the frequency of voltage produced in the piezoelectric actuator is not very high, and the quantity of current is not abruptly increased.

Even though the values of instantaneous current and instantaneous voltage vary according to the applied external force, the instantaneous current and the instantaneous voltage serve as electric stimulus through the sole, and are harmless to the body. Thus, they do not need careful consideration.

If necessary, in order to filter such instantaneous current and instantaneous voltage, a sufficient filtering effect is achieved merely by adding a general capacitor.

According to the second embodiment of this invention, the micro-current generating part 100 produces micro current in a micro-current generating circuit 120, using power supplied from a battery 110.

Figure 10:
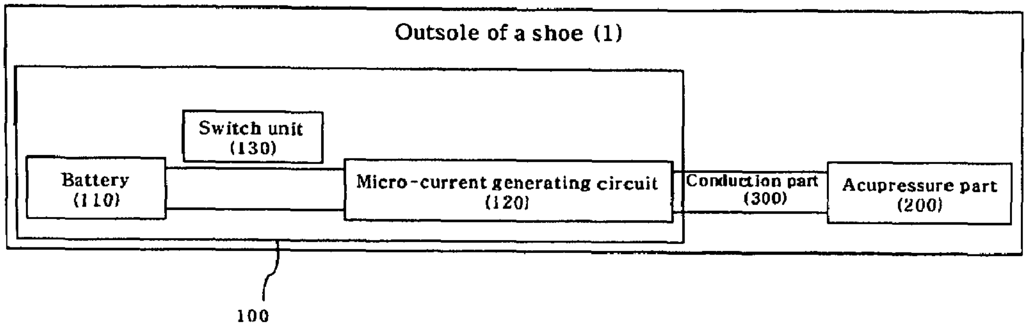
FIG. 10 is a view illustrating the concept of a functional shoe, according to the second embodiment of the present invention.
Figure 11:
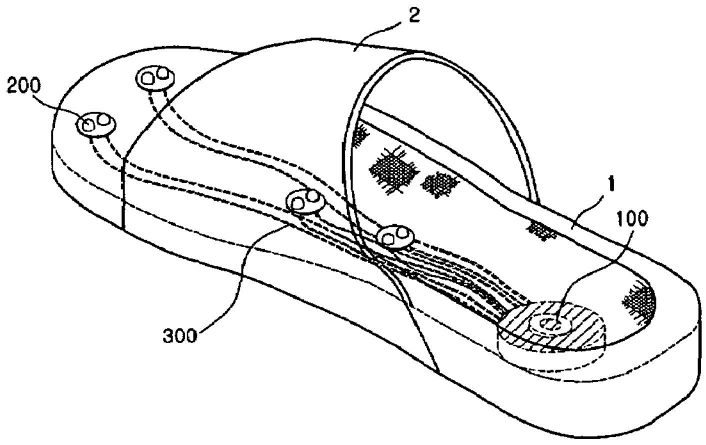
FIG. 11 is a perspective view showing the interior of the functional shoe, according to the second embodiment of this invention.
Figure 12:
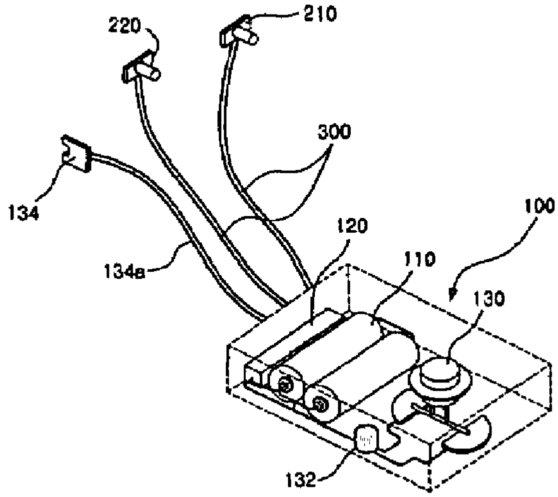
FIG. 12 is a perspective view showing a functional part of FIG. 11.

FIG. 10 is a view illustrating the concept of a functional shoe, according to the second embodiment of the present invention, FIG. 11 is a perspective view showing the interior of the functional shoe, according to the second embodiment of this invention, and FIG. 12 is a perspective view showing a functional part of FIG. 11.

Referring to FIG. 10, the micro-current generating part 100, according to the second embodiment of this invention, includes a battery 110, a micro-current generating circuit 120, and a switch unit 130. The battery 110 supplies power. The micro-current generating circuit 120 is electrically connected to the battery 110, and converts the supplied power to micro current. The switch unit 130 is connected between the battery 110 and the micro-current generating circuit 120, and controls the power supply by external force.

First, the battery 110 will be described below.

As shown in FIGS. 11 and 12, the battery 110 is installed in a heel portion of a shoe, and serves to supply power to the micro-current generating circuit 120.

Anything may be used as the battery 100 as long as it supplies power. Various batteries including a primary battery and a secondary battery may be used. The primary battery is a disposable item which is disposed after a single use, and includes a manganese battery and an alkaline battery. The secondary battery is a rechargeable battery which may be reused after being charged, and includes a nickel-cadmium battery, a nickel-hydrogen battery, and a lithium-ion battery.

According to the present invention, as shown in the drawings, the battery 110 is a general 1.5V battery. However, the battery 110 may be a rechargeable battery which may be charged using utility power.

Next, the micro-current generating circuit 120 will be described below.

The micro-current generating circuit 120 comprises a circuit board which generates micro current of several to several hundreds of micro-amperes (μA), using the power input from the battery 110. The micro-current generating circuit 120 is mounted in a case 100*a* made of synthetic resin, and is stored in a storage part provided in the heel portion of the shoe, together with the battery 110.

Further, the micro-current generating circuit 120 electrically connects a lead wire drawn from the interior of the case 100*a*, to an acupressure part 200 provided on a surface contacting the sole. When the switch unit 130 connected to the battery 110 is grounded by the force of the sole, DC power is supplied from the battery 110.

Figure 13:
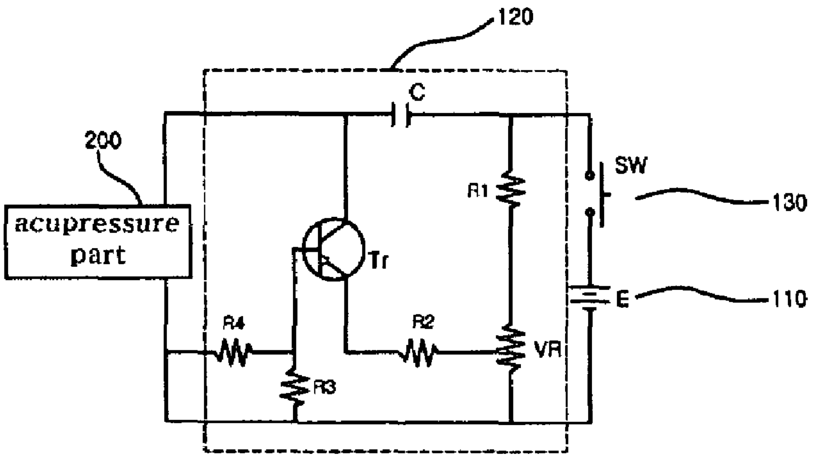
FIG. 13 is a view showing an electric circuit of a micro-current generating part, according to the second embodiment of the present invention.

As shown in FIG. 13, the battery 110 of the micro-current generating part 100 is connected to a condenser C, resistors R1-R2, a transistor Tr, and a variable resistor VR. Thus, power E of the battery 110 is supplied via the switch unit 130 to the acupressure part 200.

In this case, the micro-current generating circuit 120 generates micro current of 300 μA or less by transmitting DC power from the battery 110 through the resistors R1-R2 and the variable resistor VR, and conducts the micro current to the acupressure part 200.

In this case, the battery 100 may comprise 1.5V batteries which are arranged in series so as to supply DC power from 3 to 12V.

Further, when the width of the variable resistor VR is changed, it is possible to supply proper micro current of 300 μA or less.

Such a micro-current generating circuit 120 is operated as follows.

When the switch unit 130 is turned on by the external force, 3V DC power supplied from the battery 110 at first flows to the variable resistor VR so as to charge the condenser C. Simultaneously, the DC power is applied through the acupressure part 200 to a collector of the transistor Tr.

However, an electric current flowing to the variable resistor VR flows to the base of the transistor Tr in proportion to the magnitude of the voltage drop occurring across the resistors R1 and R2, until the condenser C is charged. Thus, a very small quantity of current flows in the transistor Tr.

Subsequently, when the condenser C has been charged, the condenser C serves as a decoupling condenser, so that the current is applied to the base of the transistor Tr.

Thus, when the transistor Tr is turned on, micro current flows in the acupressure part 200.

In this case, resistors R3-R4 may be placed on the circuit or may not be placed on the circuit according to the set value of the micro current.

Meanwhile, according to the third embodiment of this invention, the micro-current generating circuit 120 may use the internal resistance r of the acupressure part 200 as a resistor, thus generating micro current.

That is, an acupressure rod of the acupressure part 200 is made of a conductive metallic material, such as gold or silver. However, the acupressure part is used as the resistor by increasing the internal resistance value of the acupressure rod using a metallic film.

Figure 14:
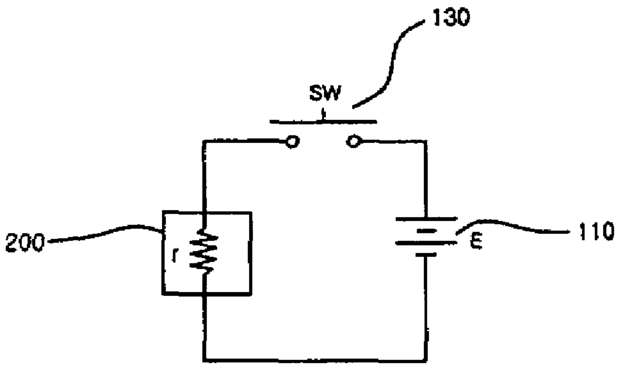
FIG. 14 is a view showing an electric circuit of a micro-current generating part, according to the third embodiment of the present invention.

Thus, as shown in FIG. 14, the present invention considers the following conditions so as to generate current of several tens of micro-amperes (μA) which is required as the internal resistance value of the acupressure part 200.

The internal resistance value of the acupressure part 200 is calculated according to the following equation.

$R=V/I$ (when a voltage V of 1V is applied and a current I of 1 A flows, the resistance R is equal to 1).

For example, assuming that the power supplied from the battery 110 is 3V, the acupressure part 200 must have an internal resistance value of 50 kΩ in order to allow micro current of 60 μA to flow.

Therefore, according to this invention, when the internal resistance value of the acupressure part 200 is changed, it is possible to supply proper micro current from 1 to 300 μA.

Figure 15:
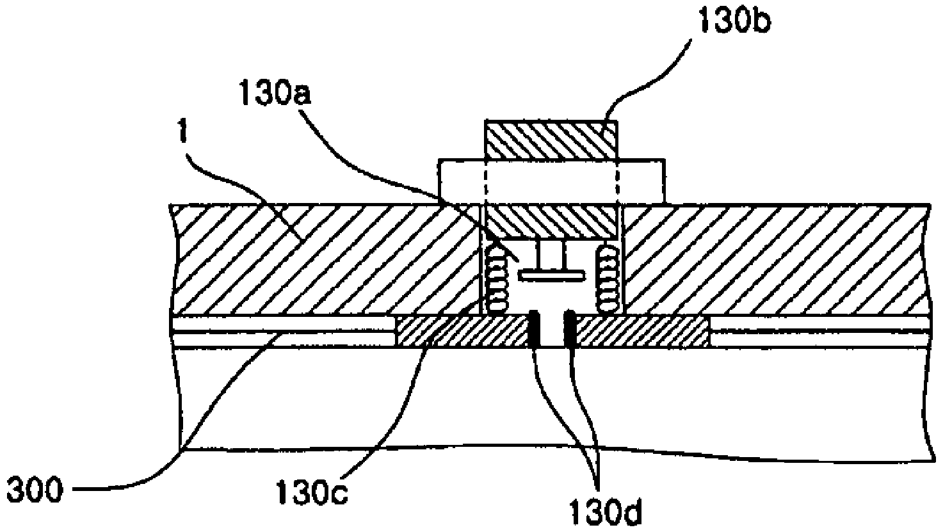
FIG. 15 is a sectional view schematically showing a switch unit 130, according to the third embodiment of the present invention.
Figure 16:
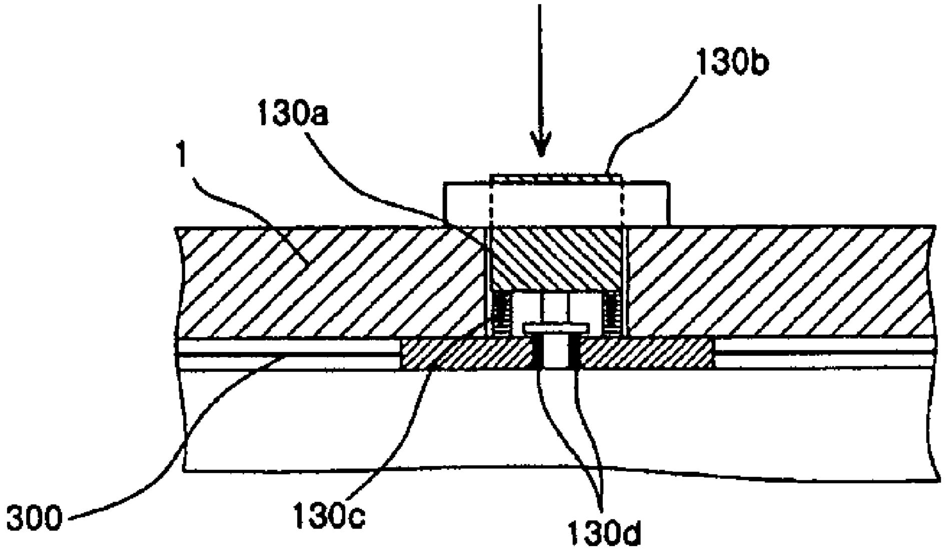
FIG. 16 is a sectional view showing the state where the switch unit 130 of FIG. 15 is pressed down and contacted by an external force.

FIG. 15 is a sectional view schematically showing a switch unit 130, according to the third embodiment of the present invention, and FIG. 16 is a sectional view showing the state where the switch unit 130 of FIG. 15 is pressed down and contacted by an external force.

Referring to FIGS. 15 and 16, the switch unit 130 includes an insert groove 130*a*, a push button 130*b*, a spring 130*c*, and a power-input contact point 130*d*. The insert groove 130*a* is formed through the heel portion of the shoe. The push button 130*b* is inserted into the insert groove 130*a*, and protrudes from the bottom surface of the shoe such that the push button 130*b* is pressed down by a user's sole. The spring 130*c* is installed between the bottom surface of the shoe and the push button 130*b*, and elastically restores the push button 130*b* to its original state when an external force is eliminated. The power-input contact point 130*d* is installed under the push button 130*b*, and is made of a conductive material.

That is, when a user wears the shoe, the push button 130*b* is pressed by the load transmitted through the sole. At this time, the switch unit 130 serves as a switch using the contact point.

As shown in FIG. 16, the external force transmitted by walking moves the push button 130*b* downwards. At this time, the push button 130*b* contacts the power-input contact point 130*d*, so that electricity is applied.

Due to such transmission of electricity, DC power of the battery 110 is transmitted to the micro-current generating circuit 120.

Thus, it is desirable that the switch unit 130 be located in the outsole or inner sole defining the shoe. The switch unit 130 may be positioned in the heel portion of the shoe or the bottom surface of the anterior region of the shoe. However, it is preferable that the switch unit 130 be positioned in the heel portion of the shoe, as shown in the drawing.

Figure 17:
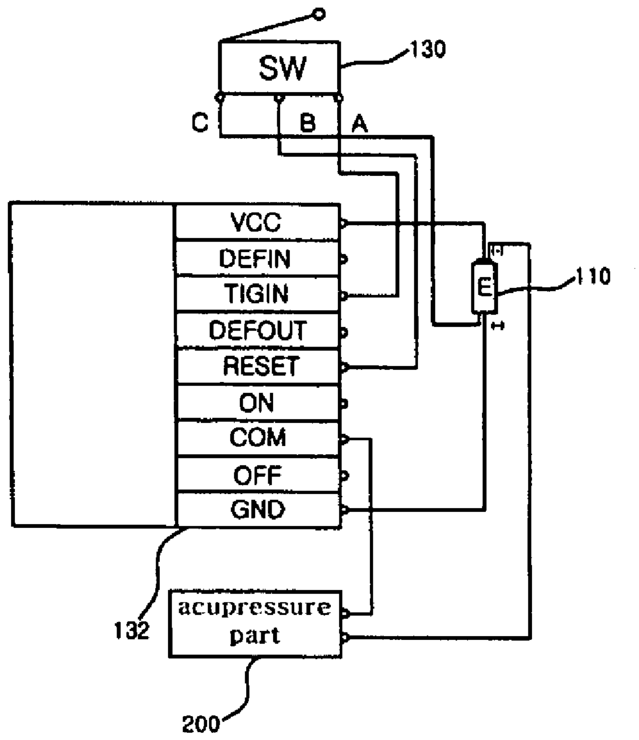
FIG. 17 is a circuit diagram of a timing circuit, according to the present invention.

Meanwhile, as shown in FIG. 17, the switch unit 130 is further provided with a timing circuit 132 which controls the driving of the micro-current generating circuit 120 according to the timing.

In this case, the timing circuit 132 is an integrated circuit wherein electricity is applied to an output port (ON/CON) for a predetermined time after the elapse of a predetermined time, when an input signal is input to a trigger port (TIGIN), and then the application of electricity is discontinued.

Further, when a signal is sent to a reset port (RESET), a timer is not operated (namely, a reset state is achieved), and electricity is not applied to the output port.

Such a switch unit 130 is a push-button-type switch which is actuated as a load detecting switch recognizing that a person's weight is applied. The switch unit 130 includes terminals A and B, and a common terminal C.

When the push button is pressed by an external force resulting from a user's load, the terminal B and the common terminal C are shorted. Meanwhile, when the push button returns to its original position, the terminal A and the common terminal C are shorted.

That is, the switch unit 130 is a state switch which forces the common terminal C to select one of terminals A and B.

Further, the common terminal C of the switch unit 130 is connected to an earth port (GND) of the timing circuit. The terminal A is connected to the trigger port (TIGIN), and the terminal B is connected to the reset port (RESET).

Thus, when the push button is connected, a signal is always sent to the reset port, the timer is not operated (that is, a reset state is achieved), and electricity is not applied to the output port.

Conversely, when the push button is restored to its original state, a signal is sent to the trigger port, and the timer starts to operate.

When the timer is operated, electricity is applied to the output port after a predetermined time has elapsed. Electricity is applied to the output port (ON/CON) for a predetermined period of time, and then application thereof to the output port is discontinued again.

At this time, the time of the timer may be selected as desired without being specifically limited.

The switch unit 130 operated in this way detects a trigger signal after the switch unit 130 contacts the battery 110. After a predetermined time has elapsed, micro current flows for a predetermined time. Thereafter, when an external force is applied, a reset signal is transmitted. When the external force is eliminated, the trigger signal is transmitted. Thereby, the driving of the micro-current generating circuit 120 can be controlled by the timing circuit 132.

Figure 18:
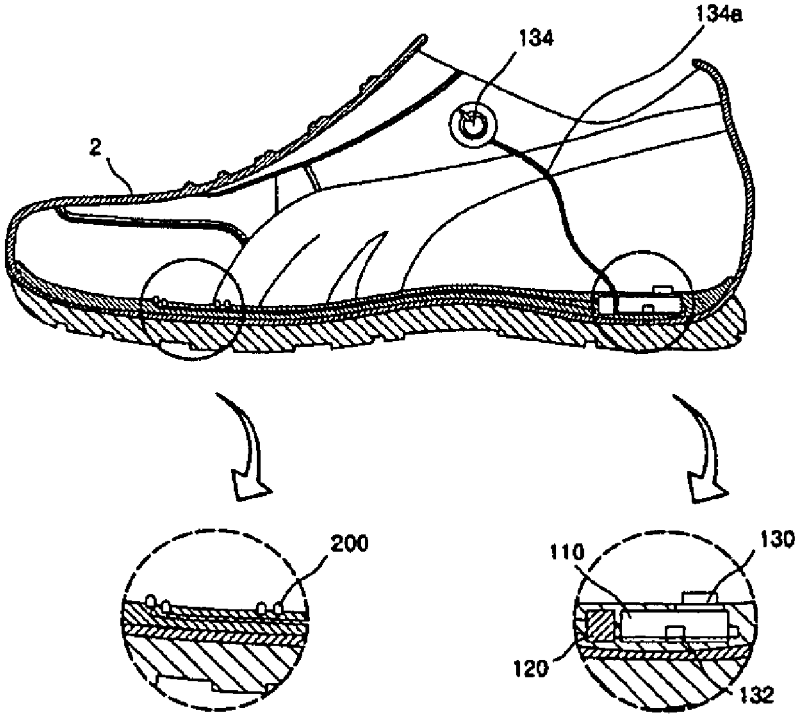
FIG. 18 is a side view of a functional shoe having a manual switch, according to the present invention.

Meanwhile, according to the preferred embodiment of the present invention, the switch unit 130 is further provided with a manual switch 134, as shown in FIG. 18. A user can control the on/off operation of power supplied from the battery 110 to the micro-current generating circuit 120 using the manual switch 134.

Preferably, the manual switch 134 is attached to the upper 2 of the shoe so that the on/off operation of the battery 110 is easily performed while the user wears the shoe.

Figure 19:
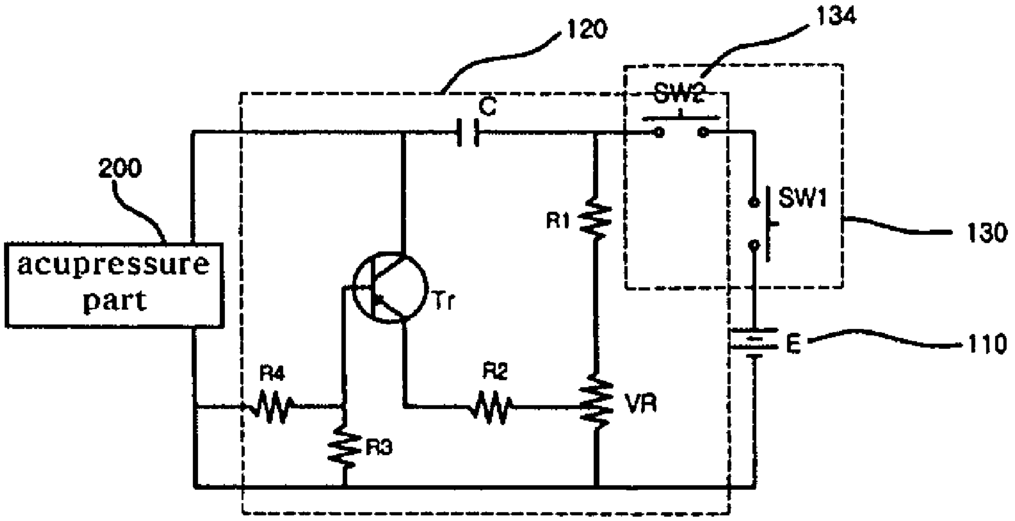
FIG. 19 is a view showing an electric circuit of FIG. 18.

Thus, as shown in FIG. 19, the supply of power from the battery 110 to the micro-current generating circuit 120 can be stopped by the manual switch 134. Thus, even if a signal of the switch unit 130 is input due to walking, the micro-current generating circuit 120 is not operated, so that undesirable power consumption of the battery 110 is prevented.

The manual switch 134 is not limited to the above construction, but may use a conventional switch structure.

Next, the acupressure part 200 and the conduction part 300 according to the present invention will be described below.

First, the acupressure part 200 will be described.

The acupressure part 200 serves to stimulate the sole using micro current, which is generated from the micro-current generating part 100 and is supplied through an electric wire.

As shown in FIG. 1, the acupressure part 200 is provided at a position at which nerve points on the sole corresponding to respective organs in the body are provided.

The acupressure part 200 is made of a conductive material, so that micro current generated from the micro-current generating part 100 flows.

Thus, physical acupressure from the acupressure part 200 and the electric stimulus of micro current are transmitted to the nerve points of the sole.

Preferably, the acupressure part 200 may be in the form of a magnet so that a magnetic field is formed by the acupressure part 200.

In this case, the nerve points distributed on the sole are stimulated by complex physical energy consisting of the physical acupressure through the acupressure part 200, the electric stimulus through the micro current, and the magnetic field, thus promoting blood circulation, therefore being helpful to various organs in the body.

Next, the conduction part 300 will be described below.

The conduction part 300 is a kind of connection part which transmits micro current generated from the micro-current generating part 100 to the acupressure part 200. The acupressure part 200 and the micro-current generating part 100 may be connected in parallel or in series.

Figure 20:
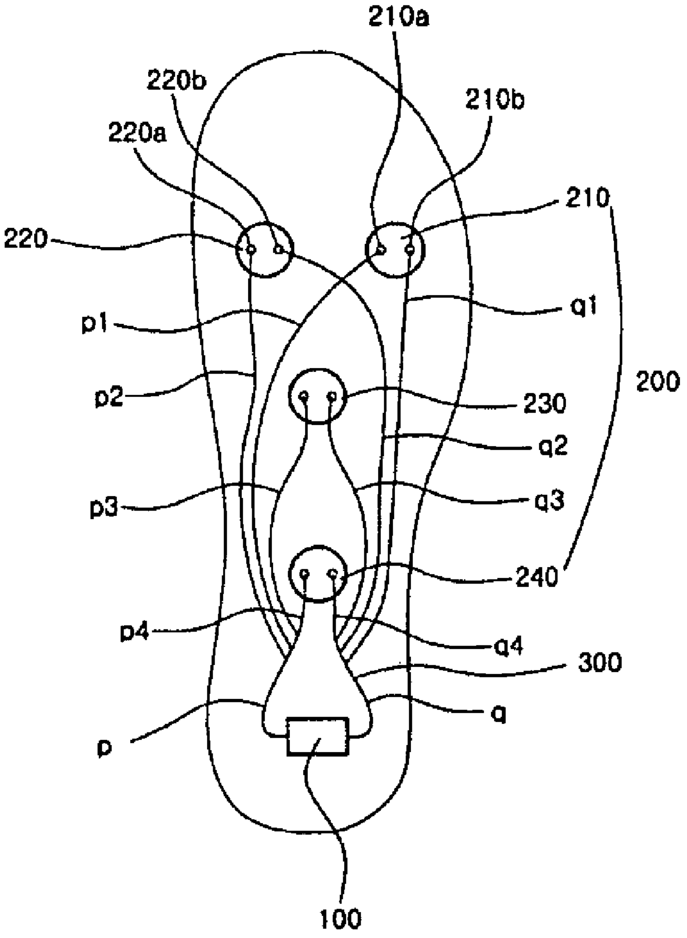
FIG. 20 is a view showing a conduction part having a parallel connection structure, according to the present invention.
Figure 21:
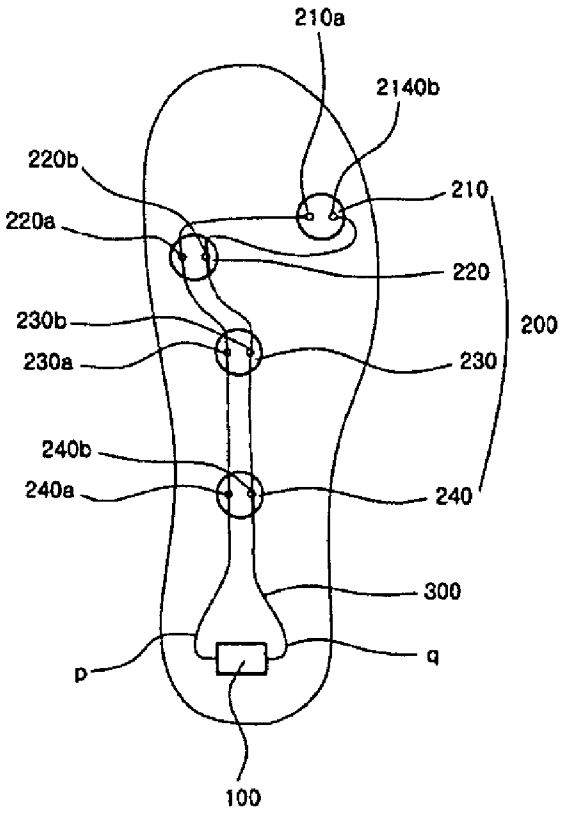
FIG. 21 is a view showing a conduction part having a series connection structure, according to the present invention.

FIG. 20 shows the parallel connection structure of the conduction part 300, and FIG. 21 shows the series connection structure of the conduction part 300.

As shown in FIG. 20, when the conduction part 300 has the parallel connection structure, constant voltage is applied to respective acupressure parts, but different currents are applied to the respective acupressure parts.

In this case, the acupressure part 200 forms an open circuit along with the micro-current generating part 100.

An electric wire p coming out from one side of the micro-current generating part 100 branches into lines p1, p2, p3, and p4 to correspond to the desired number of acupressure parts. An electric wire q coming out from the other side of the micro-current generating part 100 branches into lines q1, q2, q3, and q4 to correspond to the desired number of acupressure parts. Each branched line is connected to the acupressure rod of each acupressure part 200.

That is, the lines p1 and q1 branching from the micro-current generating part are connected to two acupressure rods 210*a* and 210*b* of a first acupressure part 210. The branched lines p2 and q2 are connected to two acupressure rods 220*a* and 220*b* of a second acupressure part 220.

Such a connection structure is a structure in which the acupressure parts are connected in parallel.

Thus, voltage applied to each acupressure part 200 is the total voltage. Micro current i1, i2, i3, i4 resulting from division of total current (I=i1+i2+i3+i4) flows in each acupressure part 200.

Meanwhile, since the acupressure rod of each acupressure part 200 is connected to a lead wire, an open circuit is formed.

In the case of the first acupressure part 210, when the sole contacts the surface of the first acupressure part 210, the micro current flows through one acupressure rod 210*a* into the sole, and thereafter flows out through another acupressure rod 220*a*.

Thus, current concentrates on the nerve point corresponding to the lung, at which the first acupressure part 210 is located, thus performing electric stimulus.

Unlike the above-mentioned case, FIG. 21 shows a structure where the conduction part 300 is connected in series.

When the conduction part 300 has a series connection structure, a line p branching from one side of the micro-current generating part 100 is connected through each acupressure part 200 to another line q of the micro-current generating part 100.

That is, the line p of the conduction part 300 is connected from one acupressure rod of the first acupressure part 210 to another acupressure rod 210*b* thereof. The line q extending from the acupressure rod 210*b* is connected from one acupressure rod 220*a* of a second acupressure part 220 to another acupressure rod 220*b* thereof.

Of course, in this case, the circuit between the acupressure rod 210*a*, 220*a*, 230*a*, 240*a* and the opposite acupressure rod 210*b*, 220*b*, 230*b*, 240*b* of the acupressure part 210, 220, 230, 240 is electrically opened.

Thus, when the sole contacts each acupressure part, a closed circuit is formed so that the sole is electrically connected to each acupressure rod. Thereby, micro current is transmitted through the acupressure rod of each acupressure part 200 to a specific portion of the sole.

As described above, the instantaneous voltage and the instantaneous current applied to each acupressure part 200 may be changed according to the manner of connection of the conduction part 300.

Of course, the construction of the conduction part 300 connecting the micro-current generating part 100 to the acupressure part 200 may be changed. That is, each acupressure part 200 may have a series connection structure.

Hereinafter, concrete embodiments of the present invention having the above-mentioned concept will be described below.

FIRST EMBODIMENT

Figure 22:
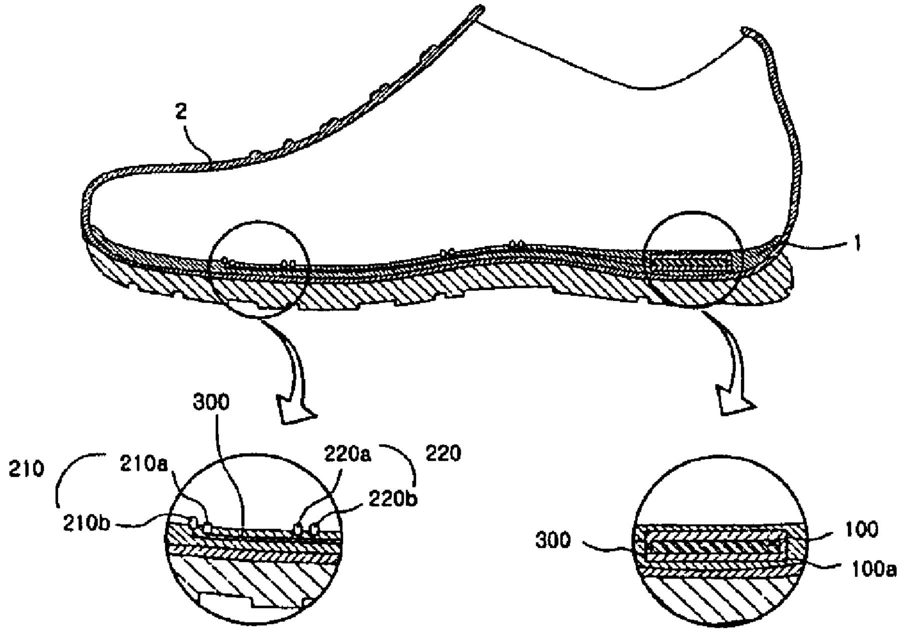
FIG. 22 is a sectional view of the functional shoe, according to the first embodiment of the present invention.

As shown in FIG. 22, according to this embodiment, a micro-current generating part 100 comprises a piezoelectric actuator, and is installed in an outsole 1 of a shoe.

That is, the micro-current generating part 100, an acupressure part 200, and a conduction part 300 are installed in the outsole 1. Such a construction is applicable to all kinds of shoes.

Thus, a shoe having the functional parts in the outsole 1 will be described below.

In the construction of the outsole 1, the micro-current generating part 100 is positioned in the heel portion of the outsole 1. The position is the position on the shoe where the highest pressure is applied.

Further, the heel portion of the shoe has the largest space, so that it is easy to install the micro-current generating part 100. The heel portion is a position which is capable of using force transmitted from the sole.

That is, according to this embodiment, pressure applied by the heel when walking is used as a power source for generating power.

Generally, when a user wearing the shoe having the micro-current generating part 100 in the outsole 1 walks, the heel of the sole contacts the ground first. Subsequently, the anterior portion of the sole contacts the ground.

Thus, the micro-current generating part 100 is located in the heel portion where the highest pressure is generated, thus maximally utilizing external force caused by walking.

Further, since the micro-current generating part 100 comprises a piezoelectric actuator manufactured by sintering piezoelectric ceramic, it may be installed in a case 100*a* made of a material having high strength, such as synthetic resin.

This prevents the piezoelectric actuator from being damaged due to repeated impact loads, and affords easy pressure transmission by the sole.

In a detailed description, the piezoelectric actuator required in the present invention has instantaneous current of several to several tens of micro-amperes (μA), and instantaneous voltage of several to several hundred volts (V), so that the piezoelectric actuator may have various sizes and shapes. However, in consideration of the shape of the heel of a shoe and ease of installation, several tens of layers of piezoelectric actuators are stacked to preferably have a size of 5 mm×5 mm×5 mm or 10 mm×10 mm×10 mm.

The outer case is formed to be slightly larger than the piezoelectric actuator, so that external force applied by the sole is transmitted through the outer case to the piezoelectric actuator, thus preventing damage to the piezoelectric actuator and allowing external force to be effectively transmitted.

The acupressure part 200 protrudes from the bottom surface of the outsole 1.

The acupressure part 200 is formed at a position at which nerve points corresponding to respective organs in the body are provided, as shown in FIG. 20.

According to this embodiment, the acupressure part 200 comprises four acupressure parts.

That is, a first acupressure part 210 is provided at a position corresponding to the lungs, a second acupressure part 220 is provided at a position corresponding to the thyroid gland, a third acupressure part 230 is provided at a position corresponding to the heart, and a fourth acupressure part 240 is provided at a position corresponding to the kidneys.

Of course, this embodiment has four acupressure parts 200, but may have more than four acupressure parts 200.

The acupressure part 200 is made of a conductive material to be electrically connected to the conduction part 300 which will be described later.

Further, acupressure rods provided on each acupressure part are electrically spaced apart from each other.

Anodic and cathodic lines are connected to each acupressure rod of the acupressure part 200, thus having an open-circuit structure.

When the sole contacts the first acupressure part 210, the sole surface is located between two acupressure rods. Thus, micro current fed through one acupressure rod is conducted through the sole into the foot, and then is conducted to another acupressure rod, thus forming an electric circuit.

Such a construction allows a specific portion of the sole to be effectively stimulated electrically.

Meanwhile, the acupressure part 200 may be made of a magnetic material so that the acupressure part itself is magnetic.

In this case, the micro current is generated through the upper surface of the acupressure part 200, and a magnetic field is formed in the acupressure part 200 itself, thus allowing magnetism induced from the magnetic field to be transmitted through the sole.

Next, the conduction part 300 will be described below.

The electrical connection between the micro-current generating part 100 and each acupressure part 200 may comprise a parallel connection or series connection, according to the operational characteristics of the piezoelectric actuator.

That is, the current and voltage of the piezoelectric actuator are basically determined according to the external pressure. However, as described above, the quantity of the generated current or voltage varies according to the material of the piezoelectric actuator.

Further, even though the piezoelectric actuator is made of the same material, the quantity of the generated current or voltage is varied according to the shape of the piezoelectric actuator, and according to whether the piezoelectric actuator is layered or not.

This embodiment has a parallel connection structure overall, and each acupressure part 200 forms an open circuit.

That is, one terminal of the micro-current generating part 100 is connected to one acupressure rod of each acupressure part 200, and another terminal of the micro-current generating part 100 is connected to another acupressure rod of each acupressure part 200.

Thus, each acupressure part 200 is connected to the micro-current generating part 100 in parallel, and the acupressure rods of each acupressure part 200 are electrically shorted, so that an electric circuit is formed on a surface contacting the sole.

In the case of such a parallel connection, the quantity of current flowing to each acupressure part 200 is constant. The quantity of current generated in the micro-current generating part 100 is transmitted to each acupressure part 200 without change. Conversely, the sum of voltages applied to respective acupressure parts is equal to voltage generated in the micro-current generating part 100.

Next, the operation of the functional shoe according to this embodiment constructed as described above will be described in brief.

First, when a user walks while wearing the shoe, the heel contacts the ground at first, and subsequently, the anterior portion of the shoe contacts the ground. Such an operation is repeatedly performed.

At this time, the rear axis of the shoe contacts the ground, and pressure of the user's weight is transmitted to the bottom of the shoe.

By the applied pressure, the piezoelectric actuator instantaneously forms current and voltage.

The formed current and voltage are transmitted through the conduction part 300 to each acupressure part 200 which is provided at a specific portion on the sole.

Figure 23:
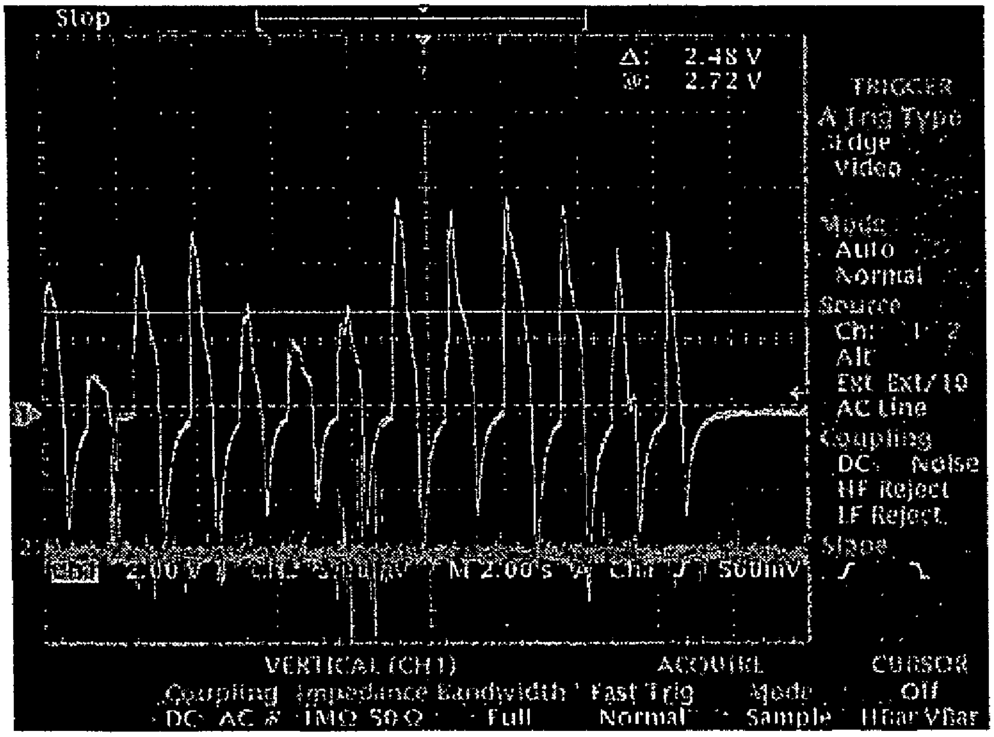
FIG. 23 is a graph showing variation in voltage when a user walks while wearing the functional shoe of this invention.

The instantaneous voltage was measured using an oscilloscope while a person weighing 60 kg wore the shoe and walked with short steps. The measured result is shown in FIG. 23.

As shown in the graph, the instantaneous voltage is produced to exceed about 10V. The current of about 2 to 10 microamperes (μA) always flows.

Meanwhile, whenever the user walks, the acupressure part 200 stimulates specific nerve points on the sole. Since the acupressure part 200 comprises a magnet, a magnetic force is transmitted through the sole to the nerve points.

At this time, the transmitted micro current is transmitted through the acupressure part 200 to the nerve points of the sole, and consequently is transmitted to the interior of the body.

The current transmitted through the acupressure part 200 is in AC form, and is several to several tens of microamperes (μA). Thus, the user cannot noticeably perceive the current, but the micro current stimulates the nerve points.

Therefore, the acupressure due to physical pressure using the acupressure part 200, the magnetic force due to the magnetic field, and the transmitted micro current are simultaneously transmitted to the nerve points, thus stimulating the nerve points. Due to the stimulus, the activity of respective organs in the body, connected to the nerve points, is strengthened, so that the stimulus is useful for the body.

SECOND EMBODIMENT

Figure 24:
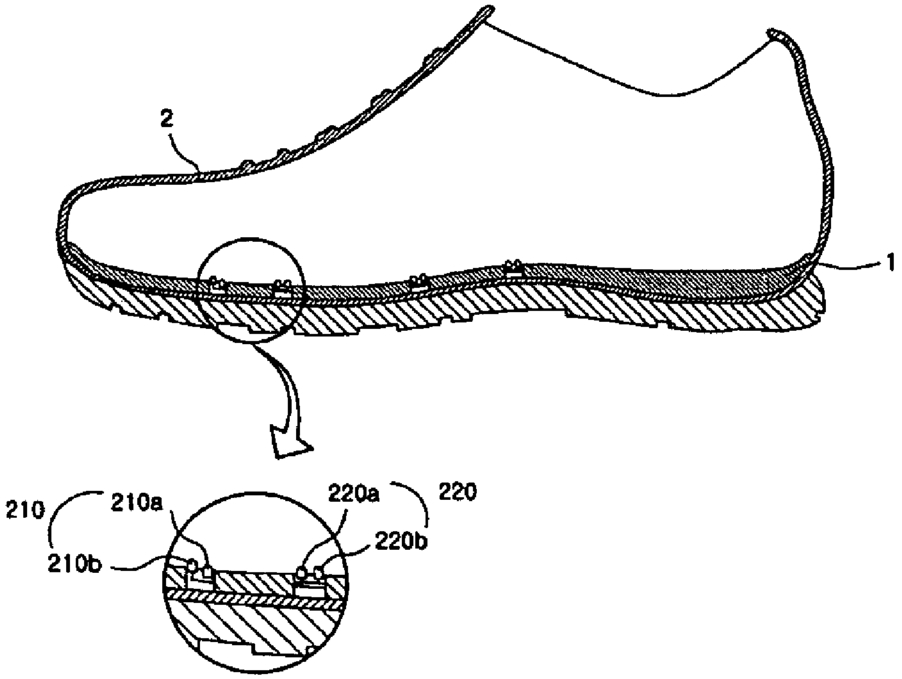
FIG. 24 is a sectional view of a functional shoe, according to another embodiment of the present invention.

As shown in FIG. 24, according to this embodiment, an acupressure part 200 is provided in an inner sole of a shoe, and the acupressure part 200 itself has a piezoelectric actuator.

That is, the piezoelectric actuator which is the micro-current generating part 100, is embedded under each acupressure part 210, 220. By the sole pressure transmitted through the acupressure parts 210 and 220, each piezoelectric actuator is driven.

To this end, the acupressure parts 210 and 220 are installed in portions where the nerve points of the sole connected to the organs in the body are located, as in the first embodiment.

Further, each acupressure part 210, 220 is made of a conductive material. Preferably, the acupressure part 210, 220 is made of a magnet having magnetism.

The piezoelectric actuator is embedded under each acupressure part 210, 220, and the piezoelectric actuator directly acts on respective nerve points. Thus, the size of the piezoelectric actuator may be slightly smaller than that of the first embodiment.

Further, one terminal p of the piezoelectric actuator is connected to one acupressure rod 210*a* of the acupressure part 210, and another terminal q of the piezoelectric actuator is connected to another acupressure rod 210*b* of the acupressure part 210.

Thus, in such a construction, the current and voltage are produced by the pressure transmitted through each acupressure part 210, 220 of the sole, and the produced current and voltage are directly transmitted through each acupressure part 210, 220.

THIRD EMBODIMENT

As shown in FIG. 18, according to this embodiment, a micro-current generating part 100 includes a battery 110, a micro-current generating circuit 120, and a switch unit 130. The micro-current generating part 100 is provided in a shoe sole 1, and so is applicable to all kinds of shoes.

That is, according to this embodiment, as a switch applying micro current, the load applied by the sole when walking is used as a contact point of the switch unit.

Further, the battery 110 and the micro-current generating circuit 120 are housed in an outer case 100*a* which is made of a synthetic resin material to have high strength, so that the damage to the battery 110 and the micro-current generating circuit 120 due to repeated impact loads is prevented.

Further, a manual switch 134 which controls the supply of power from the battery 110 is embedded in an upper 2 and connected to a lead wire 134*a*.

That is, the manual switch 134 is installed on the upper 2 of the shoe, and the lead wire 134*a* passes between the upper 2 of the shoe and cloth provided inside the upper and connected to the battery 110.

Thus, when a user presses the manual switch 134 provided on the upper, the on/off operation of the battery 110 can be controlled.

Therefore, when a user wears the shoe on a rainy day or exercises with the shoe on, he or she can control the transmission of micro current.

Meanwhile, since an acupressure part 200 and a conduction part 300 according to the third embodiment are the same as those of the above-mentioned embodiments, they will not be described herein.

Next, a functional shoe according to the third embodiment constructed as described above will be described in brief.

First, when a user walks with the shoe on, the heel contacts the ground, and subsequently the anterior portion contacts the ground. Such a motion is repeatedly performed.

At this time, while the heel of the shoe contacts the ground, a load resulting from the user's weight is transmitted to the bottom surface of the shoe.

When the push button of the switch unit 130 is pressed down and closed by the applied load, the battery 110 supplies 3V power to the micro-current generating circuit 120. The micro-current generating circuit 120 generates micro current of 60 μA, and transmits the micro current to the acupressure part 200.

That is, the contact of the switch unit 130 is repeated through the same operation due to the user's walk. Whenever the push button moves down once, micro current is applied once.

Meanwhile, a functional shoe according to another preferred embodiment of this invention is constructed such that micro current flows at an interval of 10 seconds due to control of the timing circuit 132 of the switch unit 130.

That is, when the switch unit 130 is contacted by external force, micro current only flows for 10 seconds. When an external force is applied again, the micro current flows for 10 seconds again in response to a reset signal.

By adjusting timing in this way, it is possible to reduce the supply power of the battery 110 by half or more. Further, the micro current does not flow irregularly, but flows according to a preset timing.

The micro current transmitted through the acupressure part 200 is in direct current form, and is about 60 μA. Thus, a user does not perceive the current through the senses, but the micro current continues to stimulate nerve points.

Thus, the acupressure resulting from the physical load applied by the acupressure part 200, the magnetic force formed by a magnetic field, and the transmitted micro current are simultaneously transmitted to nerve points, thus stimulating the nerve points. Such stimulus strengthens the activity of respective organs in the body connected to the nerve points, thus being useful for the body.

Hereinbefore, the embodiments adapted to shoes were described. The shoes may have various constructions.

That is, jogging shoes and exercise shoes are usually constructed so that an inner sole is additionally put in the bottom interior surface of a shoe.

In this case, like the construction of the embodiments, the functional part is integrally provided in the inner sole of the shoe. Thus, the functional part is separately manufactured without regard to a conventional shoe manufacturing process, so that the inner sole having the functional part is laid in the conventional shoe.

In contrast with such a construction, the functional part may be integrated with a shoe.

In the case of a shoe having no inner sole, such as slippers, the functional part is installed in an outsole. Further, in the case of a sports shoe, the functional part may be installed in a midsole.

Further, the electrical construction of transmitting current from the battery 110 to the acupressure part 200 may be variously changed without being limited to the above-mentioned construction.

As described above, the present invention provides a functional shoe, which is applied to various shoes, including sports shoes and dress shoes, and affords effects useful for the body, thus being widely applicable in the shoe industry.

Further, the functional shoe according to the present invention is used for a special purpose, that is, as a therapeutic shoe.

What is claimed is:

1. A functional shoe, comprising:

a micro-current generating part inserted in a side of the shoe, thus generating predetermined micro current and voltage;

an acupressure part made of a conductive material, and provided on a portion where nerve points of a sole connected to organs in a body are located, thus simultaneously performing physical acupressure action and conduction of micro current; and a conduction part connected between the micro-current generating part and the acupressure part, thus transmitting the generated micro current and voltage to the acupressure part.

2. The functional shoe according to claim 1, wherein the micro-current generating part comprises a piezoelectric actuator which instantaneously generates micro current and voltage using external force.

3. The functional shoe according to claim 2, wherein the micro-current generating part generates instantaneous current of 300 μA or less and instantaneous voltage of 50V or less, when an instantaneous external force of 3 kg to 150 kg is applied.

4. The functional shoe according to claim 2, wherein the piezoelectric actuator is provided under the acupressure part, and is connected to the acupressure part via the conduction part.

5. The functional shoe according to claim 1, wherein the micro-current generating part comprises:

a battery to supply DC power;

a micro-current generating circuit to convert the DC power supplied from the battery into micro current; and a switch unit protruding from a predetermined portion on a bottom surface contacting a sole, pressed by an external force, and performing a switching operation at predetermined timing by the external force, thus controlling power supplied from the battery to the micro-current generating part, at an exterior.

6. The functional shoe according to claim 5, wherein the micro-current generating circuit is constructed so that power supplied from the battery is electrically connected to a condenser, resistors, and a variable resistor, so that, when the switch unit is turned on by an external force, the power supplied from the battery flows to the variable resistor to charge the condenser, and simultaneously is applied to a collector of the transistor, and current flowing to the variable resistor flows to a base of the transistor in proportion to a voltage drop occurring in the resistors until the condenser is charged, and thereafter, when the condenser has been charged, the condenser serves as a decoupling condenser, so that current is applied to the base of the transistor, thus generating micro current.

7. The functional shoe according to claim 5, wherein the micro-current generating part generates micro current using internal resistance of the acupressure part.

8. The functional shoe according to claim 5, wherein the switch unit comprises:

an insert groove formed through a side of an outsole of the shoe;

a push button inserted into the insert groove, and protruding from a bottom surface of the outsole so that the push button is moved up and down by a user's sole;

a power-input contact point installed under the push button, and made of a conductive material; and a spring installed between the outsole and the push button, thus elastically restoring the push button to an original state thereof, when the external force is eliminated.

9. The functional shoe according to claim 5, wherein the switch unit further comprises:

a timing circuit detecting a trigger signal when the switch unit has contacted the battery, and detecting a reset signal when a predetermined time has passed, micro current flows for a predetermined time, and an external force is applied, thus resetting a timer operation, whereby when the external force is applied, the reset signal is sent, and when the external force is removed, the trigger signal is sent, so that the driving of the micro-current generating part is controlled by the timing circuit.

10. The functional shoe according to claim 5, wherein the switch unit further comprises:

a manual switch provided at an upper on an outer surface of the shoe, and controlling power supply from the battery.

11. The functional shoe according to claim 1, wherein the micro-current generating part is provided on a heel portion of the shoe.

12. The functional shoe according to claim 1, wherein the acupressure part comprises a magnet, thus providing stimulus using magnetism.

13. The functional shoe according to claim 1, wherein the conduction part connects the micro-current generating part to the acupressure part in parallel.

14. The functional shoe according to claim 1, wherein the conduction part connects the micro-current generating part to the acupressure part in series.

15. A functional shoe, comprising:

a main body; and an inner sole, comprising:

a micro-current generating part comprising a piezoelectric actuator which instantaneously generates micro current and voltage using external force;

a plurality of acupressure parts made of a conductive material, and provided on portions corresponding to nerve points of a sole connected to organs in a body; and a conduction part connected between the micro-current generating part and each of the acupressure parts, thus transmitting the generated micro current and voltage to each of the acupressure parts, whereby the inner sole is detachably mounted to the main body, and simultaneously performs physical acupressure action on specific nerve points of the sole and transmits micro current to the nerve points using external force applied when a user wears the shoe.

16. The functional shoe according to claim 15, wherein the piezoelectric actuator is provided under each of the acupressure parts, and is individually connected to each of the acupressure parts via the conduction part.

17. The functional shoe according to claim 15, wherein each of the acupressure parts comprises a magnet, thus providing stimulus using magnetism.

18. A functional shoe, comprising:

an outsole integrally comprising:

a micro-current generating part comprising a piezoelectric actuator which instantaneously generates micro current and voltage using external force;

a plurality of acupressure parts made of a conductive material, and provided on portions at which nerve points of a sole connected to organs in a body are located; and a conduction part connected between the micro-current generating part and each of the acupressure parts, thus transmitting the generated micro current and voltage to each of the acupressure parts, thus simultaneously performing physical acupressure action on specific nerve points of the sole and transmitting micro current to the nerve points using external force applied when a user wears the shoe.

19. The functional shoe according to claim 18, wherein the piezoelectric actuator is provided under each of the acupressure parts, and is individually connected to each of the acupressure parts via the conduction part.

20. The functional shoe according to claim 18, wherein each of the acupressure parts comprises a magnet, thus providing stimulation using magnetism.

* * * * *